United States Patent [19]

Rauscher et al.

[11] 4,267,827
[45] May 19, 1981

[54] VENTILATOR APPARATUS FOR LIFE-SUPPORT AND LUNG SCAN

[75] Inventors: L. Andrew Rauscher, Rancho Sante Fe; Donald G. Parsons, San Diego, both of Calif.

[73] Assignee: The Regents of the Univ. of California, Berkeley, Calif.

[21] Appl. No.: 84,129

[22] Filed: Oct. 12, 1979

[51] Int. Cl.³ .............................................. A61B 6/00
[52] U.S. Cl. ................................ 128/1.1; 128/205.15
[58] Field of Search ........... 128/659, 654, 1.1, 203.12, 128/205.13–205.18, 203.28

[56] References Cited

U.S. PATENT DOCUMENTS

| | | | |
|---|---|---|---|
| 3,769,967 | 11/1973 | Jones et al. | 128/654 |
| 3,881,463 | 5/1975 | LeMon | 128/654 |
| 3,890,959 | 6/1975 | Yondin et al. | 128/654 |
| 4,076,021 | 2/1978 | Thompson | 128/205.18 |
| 4,202,345 | 5/1980 | Farella et al. | 128/654 |

Primary Examiner—Henry J. Recla
Attorney, Agent, or Firm—Brown & Martin

[57] ABSTRACT

Two identical bag-in-bottle bellows assemblies are provided for separately receiving and discharging breathable oxygen/air and oxygen/air/Xenon gas mixtures. An adjustable piston/cylinder gas pump is connected with the bellows assemblies through a system of conduits and valves for selectively operating the bellows of either assembly. Hoses are interconnected between the bellows and a patient mask to form inspiratory and expiratory paths. The expiratory path includes a PEEP valve, a pressure actuated exhalation valve, an $O_2$ concentration analyzer, and a $CO_2$ absorber. The apparatus is capable of being instantaneously switched between the isolated oxygen/air and oxygen/air/Xenon delivery systems while continuously ventilating the patient and maintaining ventilation parameters (ventilation rate, inspiratory time, oxygen concentration, end-expiratory pressure, and tidal volume) substantially constant.

6 Claims, 2 Drawing Figures

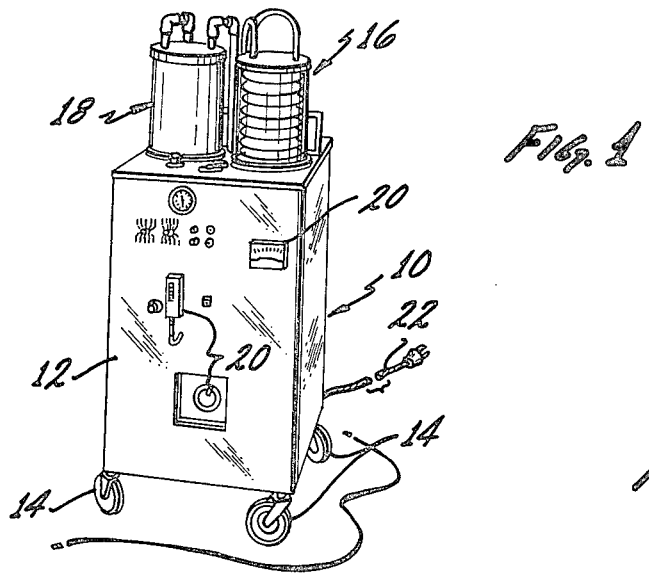
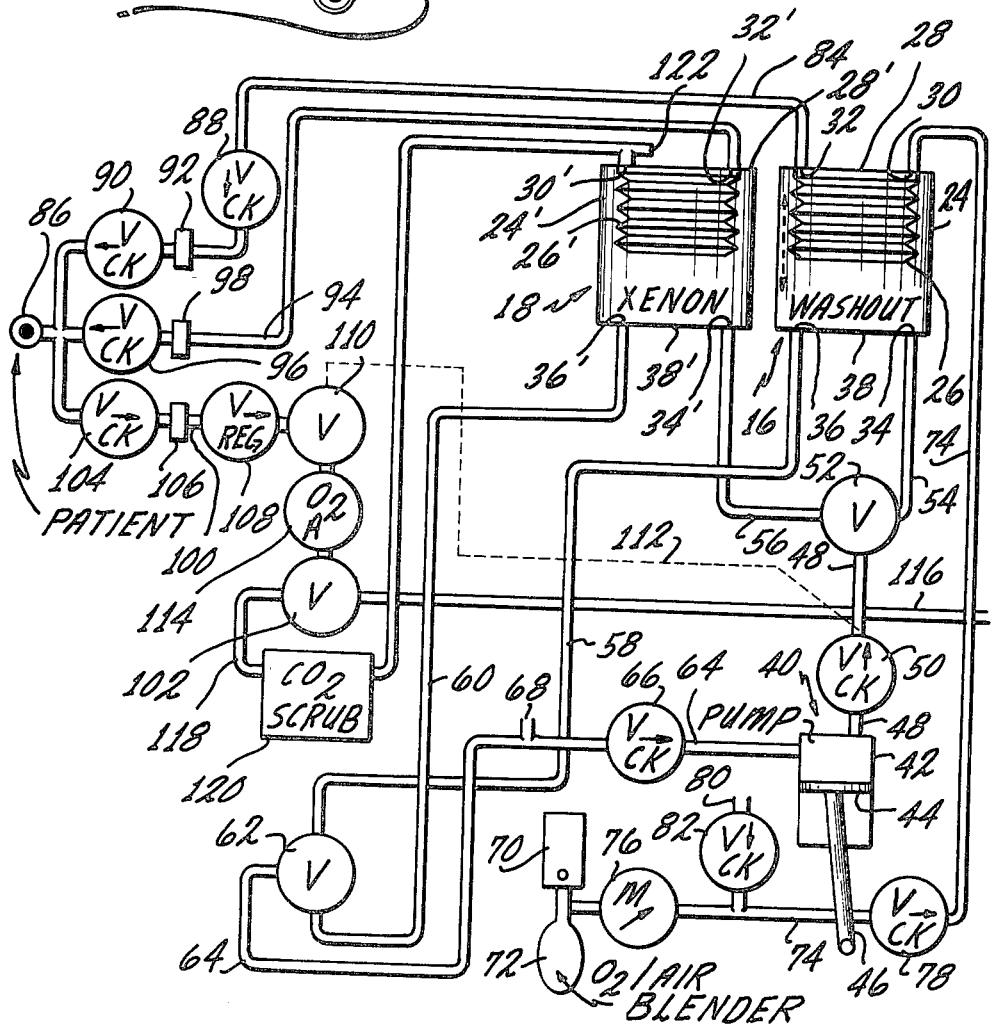

VENTILATOR APPARATUS FOR LIFE-SUPPORT AND LUNG SCAN

BACKGROUND OF THE INVENTION

The invention described herein was made in the course of, or under, a grant from the U.S. Public Health Service.

The present invention relates to apparatus for mechanically inducing inspiration and expiration in a patient. The invention further relates to ventilation/perfusion scans using scintimetric methods for diagnosis of abnormalities in the lungs. More particularly, the present invention relates to a ventilator apparatus which can be instantaneously switched between isolated oxygen-/air and oxygen/air/Xenon delivery systems while continuously ventilating the patient and maintaining ventilation parameters constant. As used herein, the term ventilation parameters includes the ventilation rate, inspiratory time, oxygen concentration, end-expiratory pressure, and tidal volume.

Ventilation/perfusion scans utilizing scintimetric methods for diagnosis of abnormalities in the lungs have been available as a diagnostic tool for some time. A ventilation scan is utilized to determine ventilatory patterns in the lungs. A perfusion scan is usually also performed at the same time to determine intrapulmonary shunting.

The combined ventilation/perfusion scan is usually performed in the following manner. During a so-called "wash-in period" the patient breathes a suitable gaseous mixture containing a traceable gas, usually a radioactive isotope such as Xenon$^{133}$, until an equilibrium state is reached at which there is a uniform concentration of the traceable gas throughout the lungs. During the wash-in period, a radiation detecting apparatus is utilized to generate a scintrimetric picture of the radioactive isotope as it spreads through the various regions of the lungs. The picture is in the form of an illuminated pattern. During the wash-in period, another radioactive isotope, for example Technetium in the form of microspheres, is injected into the patient's blood stream. The Technetium flows through the intricate network of blood vessels in the lungs. The spread of Technetium throughout the lungs is also shown in the scintimetric picture. By observing the spread of the Xenon gas throughout the lungs, the physician can determine ventilatory patterns. Dead spaces where no ventilation occurs can be located. The pattern formed by the Technetium provides valuable information concerning intrapulmonary shunting.

During a so-called "wash-out period" the patient breathes an oxygen/air mixture until the Xenon gas is substantially eliminated from his or her lungs. The physician gains further valuable information concerning the ventilatory patterns in the lungs by observing the gradual retreat of the radioactive gas. Thus, ventilation/perfusion scanning can provide valuable geographic data on the location of ventilation/perfusion mismatch areas and the response of these areas to treatment. The technique can also be used in clinical research. For example, it may be utilized to demonstrate changes in ventilation/perfusion relationships in human beings and animals in response to various physiological and mechanical conditions.

Heretofore the use of ventilation scans with Xenon gas has been limited to those patients capable of breathing spontaneously and in whom the inspired oxygen concentration has not been critical. This is because known Xenon delivery systems require that the patient be removed from a conventional life-support ventilating apparatus in order to perform a Xenon ventilation scan. For some critically ill patients, even a momentary interruption of mechanical ventilation, or a variation in one or more of the ventilation parameters can result in further health complications and in some instances even death. Therefore, the ventilation/perfusion scanning technique has not been available to patients requiring long term, continuous mechanical breathing assistance.

However, it is well recognized that patients who require mechanical ventilation for life-support have even a greater need for ventilation/perfusion scanning than those who are capable of breathing on their own. Many critically ill patients requiring mechanical ventilation for a wide variety of reasons have ventilation/perfusion abnormalities as demonstrated by increases in intrapulmonary shunting and increases in dead-space ventilation. In order to diagnose and treat such conditions, it would therefore be desirable to have the capability of supplying Xenon gas or some other traceable gas for a short period to a patient without interrupting mechanical breathing assistance and without varying any of the ventilation parameters.

A number of problems have heretofore hampered efforts to solve this problem. First of all, the traceable gas is usually a radioactive isotope. Because of the obvious hazards associated with radioactive materials, any system for delivering Xenon or other radioactive gas to a patient must be designed to isolate this gas from the normal life-support mixture. Any such system must also prevent the radioactive gas from contaminating the atmosphere and harming other individuals. Furthermore, it is desirable to minimize the amount of time that the patient must be exposed to the radioactive gas in order to achieve a proper scan.

It is not possible to accomplish a ventilation scan merely by injecting Xenon gas into a conventional ventilator for a brief period. Such ventilators typically vent expired gas into the atmosphere and as previously explained this is unacceptable where radioactive gasses are utilized. Even if a closed loop ventilation system were to be utilized, an undue amount of time would be required in order to achieve the uniform concentration of radioactive gas required to achieve a good scintimetric picture. Furthermore, at the conclusion of such a scan, minute amounts of radioactive Xenon would remain in a closed loop system. The patient would be exposed to hazardous radiation for an undue amount of time before the radioactive gas could be absorbed in a trap or otherwise safely purged from the system.

Many critically ill patients cannot be switched to a second conventional ventilator for the purpose of accomplishing Xenon ventilation because of the possible dire consequences of any interruption in the mechanically assisted breathing. Even if the patient can withstand a brief interruption in mechanical ventilation, there is presently no way to assure that the second ventilator will maintain the ventilation parameters substantially constant. Variations in one or more of the ventilation parameters in switching between two independent conventional ventilators may have an adverse affect on the patient's condition.

Finally, if the breathable mixture supplied by the ventilator apparatus during the wash-in period does not have a uniform concentration of the radioactive gas the gradual spread of the illuminated pattern in the lungs shown in the scintimetric picture will reveal less useful information.

SUMMARY OF THE INVENTION

It is therefore an object of the present invention to provide a ventilator apparatus for extending the technique of ventilation scanning to patients who are dependent upon mechanical ventilation, and precise control of ventilation parameters.

Another object of the present invention is to provide a ventilator apparatus which can be used for long term life-supporting ventilation in one mode and for ventilation scanning in another mode.

Yet another object of the present invention is to provide a ventilator apparatus having the capabilities of simultaneously providing life-supporting ventilation together with the introduction of a gaseous radioactive isotope for lung scanning.

A still further object of the present invention is to provide a ventilator apparatus which can be instantaneously switched between isolated oxygen/air and oxygen/air/traceable gas delivery systems while continuously ventilating the patient and maintaining ventilation parameters substantially constant.

Another object of the present invention is to provide a ventilator apparatus of the aforementioned type which utilizes a single controllable motive means in order to maintain the ventilation parameters constant during the switching operation.

Another object of the present invention is to provide a ventilator apparatus of the aforementioned type which will provide a uniform concentration of the traceable gas.

Still another object of the present invention is to provide a ventilator apparatus of the aforementioned type which can be operated by a simple control system.

Finally, another object of the present invention is to provide a ventilator apparatus of the aforementioned type, which is portable.

In the embodiment of the ventilator apparatus disclosed herein two identical bag-in-bottle bellows assemblies are provided for separately receiving and discharging breathable oxygen/air and oxygen/air/Xenon gas mixtures. An adjustable piston/cylinder gas pump is connected with the bellows assemblies through a system of conduits and valves for selectively operating the bellows of either assembly. Hoses are interconnected between the bellows and a patient mask to form inspiratory and expiratory paths. The expiratory path includes a PEEP valve, a pressure actuated exhalation valve, an $O_2$ concentration analyzer, and a $CO_2$ absorber. The apparatus is capable of being instantaneously switched between the isolated oxygen/air and oxygen/air/Xenon delivery systems while continuously ventilating the patient and maintaining ventilation parameters (ventilation rate, inspiratory time, oxygen concentration, end-expiratory pressure, and tidal volume) substantially constant.

BRIEF DESCRIPTION OF THE DRAWINGS

FIG. 1 is a perspective view of one embodiment of the ventilator apparatus of the present invention; and FIG. 2 is a schematic diagram of the functional components of the ventilator apparatus of FIG. 1.

DESCRIPTION OF THE PREFERRED EMBODIMENT

Referring to FIG. 1, the illustrated embodiment 10 of the ventilator apparatus of the present invention includes an upright, rectangular box 12 made of sheet metal which is supported by 360° pivoting wheel assemblies 14. A pair of bellows assemblies 16 and 18 are mounted on the top of the box and are interconnected with other components of the gas circuit hereafter described, which are contained within the housing. Access to these latter components is gained through a hinged back panel, not shown in the drawings. Various gauges and controls 20 are mounted on the front panel of the housing so that an operator can readily control and monitor the ventilation parameters during the life-support, wash-in, and wash-out modes. A power cable 22 extends from the housing for connecting the apparatus to a conventional AC outlet. Various hoses not illustrated in FIG. 1, also extend from the housing for connecting the apparatus to external pressurized oxygen and air sources and for providing the necessary expiratory and inspiratory pathways to the patient.

The functional components of the illustrated embodiment will now be described by way of reference to FIG. 2. First and second reservoir means are provided for separately receiving different gas mixtures and discharging the same to the patient in accordance with a set of predetermined ventilation parameters when a predetermined sequence of motive forces is selectively applied thereto. Specifically, a pair of identical bellow assemblies 16 and 18 are provided. They may be the conventional bag-in-bottle type wherein each bag should have an internal volume at least equal to twice the normal tidal volume of a patient. The assembly 16 handles the oxygen/air mixture while the assembly 18 handles the oxygen/Xenon/air mixture. Both bellows assemblies are identical and for the sake of brevity only the assembly 16 will be described. Like parts of the bellows assembly 18 are indicated by the same reference numerals with a prime (') notation.

The bellows assembly 16 includes a cylindrical air tight housing 24 which surrounds and encloses an accordion-like bellows 26. The bellows 26 is suspended from the top wall 28 of the housing 24. The bellows 26 has inlet and outlet openings 30 and 32 respectively for receiving and discharging gas mixtures supplied thereto upon expansion and contraction of the bellows as indicated by the dashed arrows in FIG. 2. The housing 24 has inlet and outlet openings 34 and 36 respectively in the bottom wall 38 thereof.

Gas mixture received by the bellows 26 through its inlet opening is discharged therefrom through its outlet opening. This is accomplished by pumping a suitable gas from and to the housing through its outlet and inlet openings to expand and collapse the bellows, respectively. Typically air is pumped into and out of the housing 24 to provide the motive forces. The air can be supplied and withdrawn from the cylindrical housing 24 according to predetermined time intervals, amounts and pressures, to provide the sequence of motive forces necessary to expand and contract the bellows 26 so that the oxygen/air mixture will be discharged therefrom in accordance with predetermined ventilation parameters. One suitable bellows assembly for this purpose is the Bennett Bellows, part #0571, available through Puritan Bennett Corporation, 401 East 13th Street, Kansas City, Mo. 64106. As indicated in FIG. 2, the bellows assembly 16 receives and discharges oxygen/air mixtures for the wash-out period. The bellows assembly 18 receives and discharges the oxygen/air/Xenon gas mixture during the wash-in period. Each of the bellows 26 and 26' is capable of holding a greater volume of gas mixture when fully expanded than a single tidal volume, i.e., the volume of gas which passes through the patient's lungs during a typical respiratory cycle. Thus the bellows are only partially contracted and expanded when they are being acted upon by the controllable motive means described hereafter. This is indicated by the arrows drawn with phantom lines next to the bellows 26 in FIG. 2.

Controllable motive means are provided for generating the predetermined sequence of motive forces necessary for operating the bellows of the assemblies 16 and 18 to discharge gas mixture therefrom to the patient, in accordance with the predetermined ventilation parameters. Specifically, a gas pump 40 is utilized to selectively deliver pressurized air to either of the bellows assemblies 16 and 18. One suitable gas pump for this purpose is an Emerson 3 PV Piston Pump, manufactured by J. H. Emerson Company, Cambridge, Mass. It includes a cylinder 42 which houses a reciprocating piston 44 pivotally connected to the upper end of an arm 46. The lower end of the arm 46 is pivotally connected to a rotating crank, not shown. The crank is in turn drivingly connected to an electric motor via belts (not shown). The stroke length of the piston 44 can be altered to change tidal volume, and the rate of movement of the piston can be changed on both the compression stroke and the exhaust stroke, giving inspiratory time and rate control.

Switching means are provided for selectively applying the predetermined sequence of motive forces generated by the pump 40 to different ones of the bellows assemblies 16 and 18. Specifically, an exhaust conduit 48 extends from the cylinder 42 of the pump and has a check valve 50 connected intermediate the length thereof so that during the compression stroke of the piston 44 air can flow through the conduit 48 to a first three way valve 52. The valve 52 can be manually switched to a first position so that compressed air supplied through the conduit 48 is directed through a conduit 54 and through the inlet 34 into the housing of the bellows assembly 16. When the valve 52 is manually switched to its second position, compressed air supplied through the conduit 48 flows through a conduit 56 and through the inlet 34' into the housing of the bellows assembly 18. Thus, when the valve 52 is switched to its first position, air exhausted from the pump during the compression stroke of its piston will cause the bellows 26 to contract. When the valve 52 is switched to its second position, air supplied by the pump 40 during the compression stroke of its piston will cause the bellows 26' of the bellows assembly 18 to contract.

The motive forces generated by the pump 40 are thus transmitted to a selected one of the bellows assemblies 16 and 18 in the form of compressed air, which can be supplied to different ones of the assemblies by switching the valve 52. A pair of return conduits 58 and 60 are connected to a second three way valve 62 which in turn is connected via a conduit 64 to the intake inlet of the pump cylinder 42. A check valve 66 is connected intermediate the conduit 64 and permits gas to flow therethrough only in the direction toward the pump cylinder. The three way valve 62 can be manually switched to direct air from either return conduit 58 or 60 through the conduit 64 into the pump. It will thus be understood that by simultaneously switching the first and second three way valves 52 and 62, a different one of the bellows assemblies 16 and 18 can be made to operate.

A bleed-in inlet 68 is provided intermediate the conduit 64. During the down stroke of the piston 44, a small amount of outside air is drawn into the pump cylinder 42 through the bleed-in inlet 68 along with the air returning from one of the bellows assemblies. This prevents the bellows of the particular assembly in operation from being pulled downwardly too hard.

Means are provided for supplying the desired oxygen/air mixture to the bellows assembly 16. Oxygen and air at a suitable pressure, e.g. 50 PSI, from compressed gas source is supplied to a standard oxygen/air blender 70, and through a three liter collapsible bag 72 associated therewith. A suitable blender and bag assembly for this purpose is the MOD 5100, manufactured by Bird Corporation, Respiratory Lane, Palm Springs, Calif. 92262. This blender/bag assembly allows precise adjustment of the oxygen concentration. Oxygen/air mixture from this assembly is delivered through a feed conduit 74 to the inlet 30 of the bellows assembly 16. A flow meter 76 and a check valve 78 are connected intermediate the feed conduit 74. The check valve 78 permits the oxygen/air mixture to flow only in the direction from the blender 70 and the bag 72 toward the bellows assembly 16.

An emergency air inlet 80 having a one way check valve 82 is also connected to the feed conduit 74 intermediate its length as is conventional in ventilator apparatus. The one way valve 82 is spring loaded and opens to permit outside air to be drawn into the feed conduit 74 if there should be an interruption in the supply of the oxygen/air mixture to the patient. For example, if the supply of oxygen/air mixture to the blender should terminate because of a failure of a hospital compressor unit, the suction in the feed line 74 will cause the valve 82 to open during the inspiratory phase so that outside air can be drawn into the bellows 26.

First inspiratory path means are provided for supplying the oxygen/air mixture discharged from the first reservoir means (bellows assembly 16) to the patient. A hose 84 is connected at its one end at the outlet 32 of the bellows assembly 16. The other end of the hose 84 is connected to a conventional patient mask assembly, 86. One way check valves 88 and 90 are connected intermediate the length of the hose 84 for permitting the flow of oxygen/air mixture only in the direction from the bellows assembly 16 toward the patient. A filter 92 is also connected intermediate the hose 84 between the check valves 88 and 90. Filter 92 may take the form of a series of conventional three micron bacterial scrubbing filters.

Second inspiratory path means are provided for supplying an oxygen/air/traceable gas mixture discharged from the second reservoir means (bellows assembly 18) to the patient. A hose 94 is connected at its one end to the outlet 32' of the bellows assembly 18. The other end of the hose 94 is connected to the mask 86. A one way check valve 96 and a filter 98 are connected intermediate the hose 94 and perform the same functions as those described with regard to the first inspiratory path means.

Finally, expiratory path means are provided for receiving expired mixture from the patient. A hose 100 is connected at its one end to the mask 86 and at its other end to a third three way valve 102. Connected intermediate the hose 100 are a one way check valve 104 and a filter 106. The check valve permits expired gas mixture from the patient to flow only in the direction of from the patient to the three way valve 102. The filter 106 performs the same function as the filters 92 and 98. Valve means are associated with the expiratory path means for maintaining a predetermined positive end-expiratory pressure. For this purpose a conventional PEEP valve 108 is connected intermediate the length of the hose 100. One suitable PEEP valve is #6250 manufactured by Puritan Bennett Corporation, whose address has previously been given. This valve can be adjusted so that during the patient's expiratory phase, it will remain open until the patient's expiratory pressure falls to for example, 5 cm of water at which time it will close off the hose 100 to maintain a positive pressure in the patient's lungs. This facilitates re-inflation of the patient's lungs during the following inspiratory phase. The use of such PEEP valves in ventilator apparatus for this function is well known.

Valve means are also provided for closing the expiratory path means while gas mixture is being supplied to the patient through one of the first and second inspiratory path means and for thereafter opening the expiratory path means in accordance with the set of predetermined ventilation parameters. Specifically, a control valve 110 is connected intermediate the hose 100 and has a control pressure line 112 (shown in phantom lines in FIG. 2) connected to the exhaust conduit 48 of the piston/cylinder pump. One suitable valve for this purpose is the Bennett exhalation valve #5540, manufactured by Puritan Bennett Corporation, whose address has previously been given. It incorporates a baloon which is repeatedly inflated through the control line 112 to block the path through the hose 100 during the inspiratory phase. During the exhaust stroke of the pump 40, the baloon deflates to allow expired gas from the patient to flow through the hose 100.

Means are further provided for detecting the oxygen concentration in the expired gas mixture. For this purpose a conventional oxygen analyzer 114 is connected intermediate hose 100. It is connected to a meter (not shown) mounted on the face panel of the housing 12 (FIG. 1) so the operator can constantly monitor the oxygen concentration by observing the same.

By manually switching the three way valve 102, expired gas mixture can either be directly vented to the atmosphere through a relief line 116 or to the inlet 30' of the bellows assembly 18 via a conduit 118. Means are provided for absorbing excess carbon dioxide from the expired gas mixture which is returned to the bellows assembly 18. For this purpose a carbon dioxide scrubber 120 may be connected intermediate the conduit 118. One suitable scrubber is model #401-1001, manufactured by Dryden Corporation, 5707 Park Plaza Court, Indianapolis, Ind. The conduit 118 is provided with a traceable gas inlet 122 which may be opened to permit introduction of Xenon gas and thereafter closed. Not shown in FIG. 2 is a conventional Xenon trap which is connected to the relief line 116. It absorbs substantially all of the Xenon gas passing through it to prevent radioactive contamination of the atmosphere.

The operation of the preferred embodiment will now be described. During normal life-supporting ventilation, the pump 40 and the blender 70 are adjusted in accordance with the desired ventilation rate, inspiratory time, oxygen concentration, and tidal volume. The PEEP valve 108 is adjusted to achieve the desired end-expiratory pressure. The first and second three way valves 52 and 62 are switched so that the motive forces generated by the pump 40 are transmitted via compressed air to accomplish expansion and contraction of the bellows assembly 16 in accordance with the ventilation parameters. The third three way valve 102 is switched to connect the hose 100 with the relief line 116. During the compression stroke of the piston 44, oxygen/air mixture previously drawn into the bellows 26 is forced into the patient via the hose 84 and the mask 86. During the compression stroke of the pump, the exhalation valve 110 is closed. Thus, the patient's lungs are inflated. During the exhaust stroke of the piston 44, bellows 26 expands to draw in a new charge of oxygen/air mixture. At the same time, the exhalation valve 110 opens, and expired gas from the patient passes through the PEEP valve 108, through the oxygen analyzer 114 and into the atmosphere through the relief line 116.

In order to perform a ventilation scan on the patient, the bellows assembly 18 is charged through inlet 122 with a suitable mixture containing oxygen, air and a traceable gas such as Xenon in the volumetric range extending from a volume equivalent to one full tidal volume of a patient to a volume equivalent to the total expanded volume of the bag minus one full tidal volume of a patient. The first, second and third three way valves 52, 62 and 102 are switched so that pressurized air from the pump 40 expands and contracts the bellows of the assembly 18. The oxygen/air/Xenon mixture is discharged from the bellows 26' through the hose 94 into the patient during the compression stroke of the piston 44. During the exhaust stroke of the piston 44 expired mixture from the patient passes through the hose 100, through the PEEP valve 108, through the exhalation valve 110 to the three way valve 102. The expired mixtured flows from the valve 102 through the conduit 118 back into the bellows 26' by way of the $CO_2$ scrubber 120. At the conclusion of the wash-in period the three way valves 52, 62 and 102 are switched back to their original positions. The bellows assembly 16 once again operates to deliver oxygen/air mixture to the patient during this wash-out period.

It is to be emphasized that in switching from the normal life-support ventilation to the ventilation scan and back to the normal life-support ventilation, the ventilation parameters are maintained substantially constant, since the motive forces generated by the pump 40 remain identical and are merely switched between two identical bellows assemblies. The illustrated embodiment of the apparatus follows the same pressure versus time wave form in both its life-support and lung scan modes. The individual respiratory cycle which is actually interrupted by the switching is disrupted insofar as pressure is concerned. However, within several seconds the preselected ventilation parameters are reestablished. In effect, a phase shift of the pressure versus time wave form occurs during the switching. This momentary disruption does not pose any substantial risk to the patient being ventilated. Thus, in order to perform a ventilation scan with the disclosed apparatus, it is unnecessary to take a critically ill patient off of his or her normal life-support ventilator. There is no interruption in mechanically assisted breathing. Furthermore, in switching between normal life-support ventilation and ventilation with radioactive gas, there is no variation in the ventilation rate, inspiratory time, oxygen concentration, and expiratory pressure, and tidal volume. Thus, the patient is not adversely affected by any variation in his or her ventilation parameters. The oxygen/air and oxygen/air/traceable gas mixtures are isolated from one another. The patient need be exposed to the radioactive gas for only a short period, and upon return to ventilation through the bellows assembly 16, radioactive gasses are quickly purged from the patient's lungs. Thus, the hazards associated with exposing the patient to an undue amount of radiation are appreciably lessened.

While a preferred embodiment of the ventilator apparatus of the present invention has been described in detail, it will be apparent to those skilled in the art that the invention permits of modification in both arrangement and detail. For example, different kinds of bellows assemblies may be utilized. The valves can be solenoid operated and activated by a central control system. A fluid logic circuit may be substituted for the pump. The arrangement of conduits and valves may be widely varied. However, the present invention should be limited only in accordance with the following claims.

We claim:

1. Apparatus for ventilating patient comprising:
   controllable motive means for generating a predetermined sequence of motive forces;
   first reservoir means for receiving an oxygen/air mixture in an amount necessary for administering said mixture to a patient for both an inhalation and exhalation phase and discharging the same to the patient in accordance with a set of predetermined ventilation parameters when the predetermined sequence of motive forces is applied thereto;
   first inspiratory path means for supplying the oxygen/air mixture discharged from the first reservoir means to the patient;
   second reservoir means for receiving an oxygen/air/traceable gas mixture in an amount necessary for administering said mixture to a patient for both an inhalation and exhalation phase and discharging the same to the patient in accordance with the set of predetermined ventilation parameters when the predetermined sequence of motive forces is applied thereto;
   second inspiratory path means for supplying the oxygen/air/traceable gas mixture discharged from the second reservoir means to the patient;
   expiratory path means for receiving expired mixture from the patient; and
   switching means for selectively applying the predetermined sequence of motive forces generated by the controllable motive means to different ones of the first and second reservoir means whereby the patient is continuously ventilated and the ventilation parameters of the predetermined set are maintained substantially constant.

2. Apparatus according to claim 1 and further comprising valve means associated with the expiratory path means for maintaining a predetermined end-expiratory pressure.

3. Apparatus according to claim 1 and further comprising means associated with the expiratory path means for detecting the oxygen concentration in the expired mixture.

4. Apparatus according to claim 1 and further comprising valve means for closing the expiratory path means while mixture is being supplied to the patient through one of the first and second inspiratory path means and for thereafter opening the expiratory path means in accordance with the set of predetermined ventilation parameters.

5. Apparatus according to claim 1 and further comprising:
   means for absorbing carbon dioxide from the expired mixture;
   valve means associated with the expiratory path means for selectively directing the expired mixture to an exit vent or to the carbon dioxide absorbing means; and
   conduit means for directing expired mixture from the carbon dioxide absorbing means back into the second reservoir means.

6. Apparatus according to claim 1 wherein
   the first and second reservoir means each include a bellows having inlet and outlet openings for the mixture received thereby and a housing surrounding the bellows having inlet and outlet openings so that mixture received by the bellows through its inlet opening can be discharged therefrom through its outlet opening by pumping a gas from and to the housing through its outlet and inlet openings to expand and collapse the bellows, respectively;
   the controllable motive means includes a gas pump; and
   the switching means includes conduit and valve means for selectively interconnecting the gas pump with the housing of one of the first and second reservoir means to expand and collapse the bellows thereof.

* * * * *